United States Patent [19]
Suval

[11] Patent Number: 5,611,357
[45] Date of Patent: Mar. 18, 1997

[54] METHOD AND APPARATUS FOR TREATING VARICOSE VEINS

[76] Inventor: William D. Suval, 15201 Eleventh St., Suite 300, Victorville, Calif. 92392

[21] Appl. No.: 385,794

[22] Filed: Feb. 9, 1995

[51] Int. Cl.$^6$ .............................. A61B 19/00; A61B 17/08
[52] U.S. Cl. ............................................. 128/898; 606/158
[58] Field of Search ........................... 128/898; 606/158, 606/159, 144, 148

[56] References Cited

U.S. PATENT DOCUMENTS

| | | | |
|---|---|---|---|
| 3,954,108 | 5/1976 | Davis | 606/158 X |
| 4,058,126 | 11/1977 | Leveen | 606/158 X |
| 4,760,846 | 8/1988 | Mers Kelly et al. | 606/158 X |
| 4,827,929 | 5/1989 | Hodge | 606/158 X |
| 4,877,028 | 10/1989 | Sanhaus | 606/158 |
| 4,881,939 | 11/1989 | Newman | 606/158 X |
| 5,254,095 | 10/1993 | Harvey | 606/158 X |
| 5,282,812 | 2/1994 | Suarez et al. | 606/158 |
| 5,304,183 | 4/1994 | Gourlay et al. | 606/41 |
| 5,306,283 | 4/1994 | Conners | 606/158 X |
| 5,366,458 | 11/1994 | Korthoff et al. | 606/157 |

OTHER PUBLICATIONS

"Treatment of Long Saphenous Varicosities and Their Recurrence: A Long–Term Follow–up", by Eric P. Lofgren, M.D., Surgery of the Veins, pp. 285–321, 1985 by Grune & Stratton, Inc.

"A New Approach to Short Saphenous Vein Varicosities", by John T. Hobbs, M.D., F.R.C.S., Surgery of the Veins, pp. 301–321, 1985 by Grune & Stratton, Inc.

"Varicose Veins", by Aksel G. Nordestgaard and Russell A. Williams, Vascular Surgery Principles and Practice (Second Edition), Chapter 67, pp. 841–851, McGraw–Hill, Inc.

*Primary Examiner*—Michael Powell Buiz
*Assistant Examiner*—Nancy Connolly Mulcare
*Attorney, Agent, or Firm*—Graham & James LLP

[57] ABSTRACT

A minimally invasive method for treating a varicose vein is provided. Generally, the method includes the opening of at least one small incision through a skin layer of the patient adjacent to the varicose vein. The varicose vein is then at least partially obstructed through the small incision. Thereafter, the incision is closed by conventional techniques. More specifically, the vein is at least partially obstructed by threading a suture through the small incision that extends through at least a portion of the vein. A plurality of small incisions in close proximity with the vein are opened with at least one of the plurality of small incisions being substantially centered over the vein. The suture is threaded through the substantially centered incision so that the suture penetrates through at least a portion of the vein. The suture is then withdrawn through another one of the plurality of small incisions. Next, the suture is re-threaded through the other one of the plurality of small incisions so that the suture penetrates through at least a portion of the vein in close proximity with the portion of the vein previously penetrated by the suture. Finally, the suture is re-withdrawn through the substantially centered incision. The threading, withdrawing, re-threading, and re-withdrawing steps are repeated with respect to each other one of the plurality of small incisions.

9 Claims, 4 Drawing Sheets

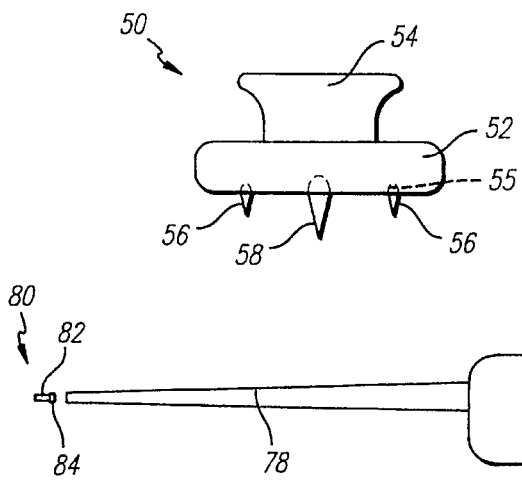
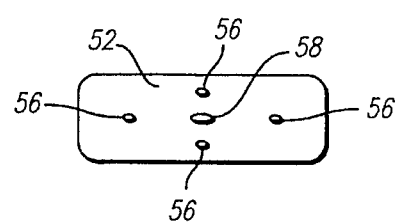
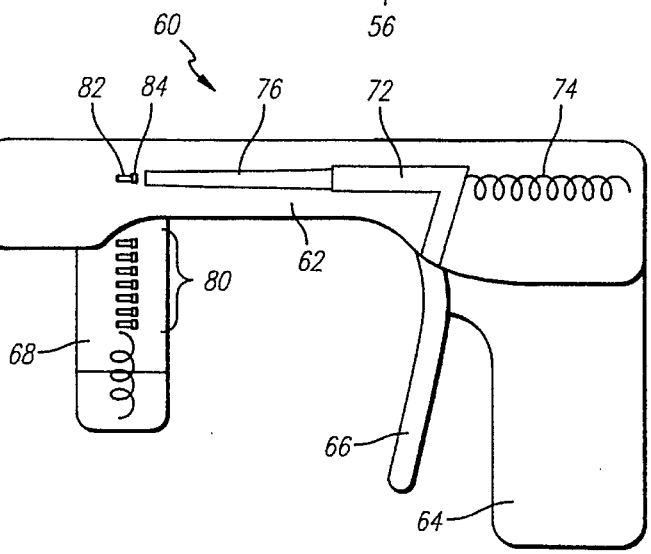
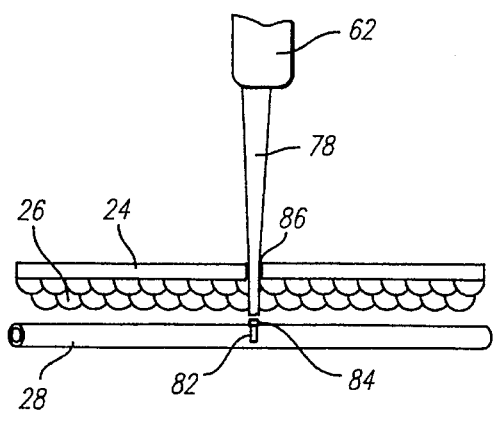
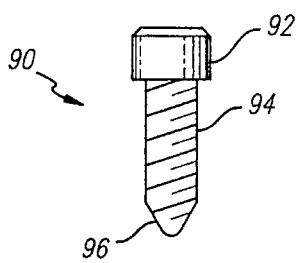
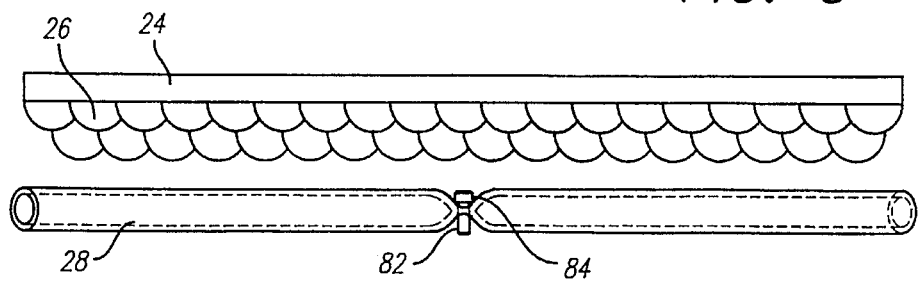

METHOD AND APPARATUS FOR TREATING VARICOSE VEINS

BACKGROUND OF THE INVENTION

1. Field of the Invention

The present invention relates to medical treatment of varicose veins, and more particularly, to a minimally invasive method and apparatus for treating varicose veins that allows for complete obliteration of the affected veins without scarring or any of the other undesirable complications of conventional treatments.

2. Description of Related Art

Varicose veins is a medical condition present in up to twenty-five percent of the adult population, and is especially prevalent among middle-aged women. The term "varicose" is derived from the Greek word for "grapelike" and refers to the torturous appearance of the afflicted veins. Patients suffering from varicose veins often experience various symptoms, including aching, itching, heaviness, swelling or cramping of the legs, while more serious complications of varicose veins can include thrombophlebitis, dermatitis, hemorrhage and ulcers. Even absent such complications, many patients seek medical treatment of varicose veins for primarily cosmetic reasons due to the generally unsightly appearance that characterizes the condition.

Specifically, varicose veins are a condition of the superficial saphenous veins of the legs in which the veins have become abnormally twisted, lengthened, or dilated. The condition is usually caused by inefficient or defective one-way valves within the veins. These one-way valves provide an important function in controlling blood pressure within the venous system of the legs. During walking, the leg muscles provide a musculovenous pump that compresses the veins and propels blood to the heart. Efficiency of the musculovenous pump is enhanced by the one-way valves within the veins that protect the venous system at the lower extremities from excess pressure generated by coughing, straining, lifting, standing or other such exertion. The superficial veins normally carry only ten to fifteen percent of the blood, with the remainder carried by the deep veins; however, the percentage of blood carried by the superficial veins can exceed these normal levels due to dilation of the superficial veins or thrombosis of the deep veins. As a result, the one-way valves can become incompetent which further increases retrograde pressure within the superficial veins. Since the superficial veins lie close to the skin layer and are poorly supported by the subcutaneous tissue, the increased retrograde pressure causes the varicose veins to be formed.

There are two known types of treatment for varicose veins. A first type of treatment comprises surgical removal of the superficial varicose veins, also referred to as "vein stripping." In the stripping technique, a surgeon first makes an incision at the groin area through which the saphenous vein is separated from the femoral vein. The saphenous vein is also dissected at the foot, and at that point, a vein stripper, such as a wire, is inserted into the lumen of the saphenous vein. The wire is then threaded through the saphenous vein to the incision at the groin. The wire includes a nut at an end thereof that catches on the foot end of the saphenous vein. The surgeon then removes the wire though the groin incision to gently extract the vein. It is further necessary to make multiple small incisions along the leg in order to disconnect the numerous tributary veins from the saphenous vein and to ligate these tributary veins. Once the saphenous vein is completely removed from the leg, the various incision wounds can be sutured closed.

The stripping technique represents a permanent solution in that the varicose vein condition cannot recur once the vein has been removed. Nevertheless, the technique has numerous significant drawbacks that render it an unsatisfactory treatment. The numerous incisions often leave substantial unsightly scars along the legs that can be as unpleasant in appearance as the original varicose vein condition. Moreover, the procedure is generally performed under general anesthesia and often requires an overnight hospital stay. There are also associated complications of the technique, such as blood loss, pain, infection, hematoma, nerve injury and swelling. After undergoing the stripping technique, a patient generally requires several weeks to recover. In view of these significant drawbacks, the stripping technique is recommended only for extreme cases of varicose veins, and for patients that are in sufficiently good health to handle the surgery.

A second technique for treating varicose veins is known as sclerotherapy. This technique involves injection of toxic fluids, such as sodium tetradecyl sulfate, into the veins to cause subsequent inflammation and sclerosis of the veins. The sclerosis results in localized scarring or closure of the veins, which forces rerouting of the blood away from the affected veins. The sclerotherapy technique is often combined with an operative procedure, such as ligation of a portion of the saphenous vein.

While the sclerotherapy technique is less surgically intensive than the stripping technique, it often does not represent a permanent or complete solution since it has a high rate of recurrence and cannot be applied to the saphenous vein in the upper thigh region due to the risk of sclerosis of the deep veins. Sclerotherapy has other potentially serious complications, including skin staining, ulceration, phlebitis, allergic or anaphylactic overdose, ischemia, skin or fat necrosis, and peripheral neuropathy. Notwithstanding these complications, patients must often undergo multiple courses of sclerotherapy treatment in order to completely alleviate the varicose veins to a satisfactory degree.

In view of these significant drawbacks of the conventional treatments for varicose veins, a critical need exists for a minimally invasive and permanent treatment for varicose veins. Such a treatment should provide for complete obliteration of the affected veins without visible scarring, excess hospitalization or any of the other undesirable complications of the conventional treatments.

SUMMARY OF THE INVENTION

In accordance with the teachings of the present invention, a minimally invasive method for treating a varicose vein is provided. Generally, the method includes four steps, including: (a) ligating the junction between the varicose vein and the deep veins of the patient's leg; (b) opening at least one small incision through a skin layer of the patient's leg adjacent to the varicose vein; (c) at least partially obstructing the varicose vein through the small incision; and (d) closing the incision by conventional techniques.

More specifically, the vein is at least partially obstructed by threading a suture through the small incision and extending through at least a portion of the vein. A plurality of small incisions in close proximity with the vein are opened with at least one of the plurality of small incisions being substantially centered over the vein. The suture is threaded through the substantially centered incision so that the suture penetrates through at least a portion of the vein. The suture is then withdrawn through another one of the plurality of small incisions. Next, the suture is re-threaded through the other one of the plurality of small incisions so that the suture penetrates through at least a portion of the vein in close proximity with the portion of the vein previously penetrated by the suture. Finally, the suture is re-withdrawn through the substantially centered incision. The threading, withdrawing, re-threading, and re-withdrawing steps are repeated with respect to at least one other one of the plurality of small incisions.

After the threading of the suture is complete, the exposed ends of the suture that extend outwardly of the vein are tied through the substantially centered incision. The exposed ends of the suture that extend outwardly of the vein through the substantially centered incision are cut off. Any portion of the cut exposed ends of the suture are prevented from extending through the substantially centered incision.

In an embodiment of the present invention, a first apparatus for use in treating a varicose vein is provided. The first apparatus comprises a substantially flat base having a plurality of receiving sockets disposed on a lower surface thereof and a handle extending from an upper surface thereof. At least one removable blade is engaged within a respective one of the receiving sockets so that the blade extends perpendicularly from the lower surface. At least one of the receiving sockets is substantially centrally disposed along an axis of the base, and has a shallower depth than other ones of the receiving sockets so that a blade disposed therein extends a greater distance from the base than other ones of the blades. The handle has a curved portion to facilitate gripping by a user.

In another embodiment of the present invention, a second apparatus for use in treating a varicose vein is provided. The second apparatus comprises a housing having a handle portion enabling gripping by a user and a needle extending axially from an end thereof. The needle has an internal passage, and is capable of injection through a skin layer of a patient and into the varicose vein. A cartridge is coupled to the housing and holds a plurality of rivets. The rivets are dimensioned to pass through the internal passage. One of the rivets is driven through the passage and into the varicose vein upon intentional triggering by the user. Thereby, the varicose vein is at least partially obstructed by the rivet.

A more complete understanding of the method and apparatus for treating varicose veins will be afforded to those skilled in the art, as well as a realization of additional advantages and objects thereof, by a consideration of the following detailed description of the preferred embodiment. Reference will be made to the appended sheets of drawings which will first be described briefly.

BRIEF DESCRIPTION OF THE DRAWINGS

FIG. 5 is a side view of a multiple incision tool of the present invention;

FIG. 6 is a bottom view of the incision tool of FIG. 5;

FIG. 7 is a side cross-sectional view of a rivet injecting tool of the present invention;

FIG. 8 is a cross-sectional view of a skin layer and superficial vein under treatment by the rivet injecting tool of FIG. 7;

FIG. 9 is a cross-sectional side view as in FIG. 8, illustrating a superficial vein obstructed by a rivet; and FIG. 10 is an enlarged perspective view of a threaded rivet for obstructing a superficial vein.

DETAILED DESCRIPTION OF THE PREFERRED EMBODIMENT

Figure 1:
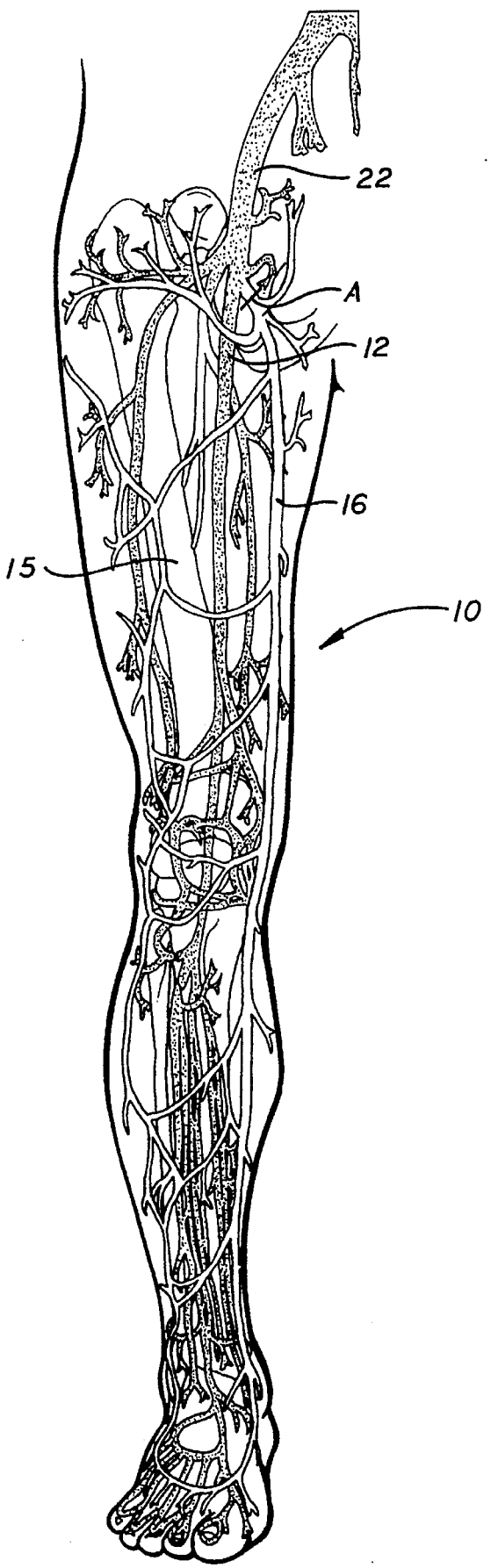
FIG. 1 illustrates a leg showing the superficial and deep venous systems.

The present invention overcomes the significant drawbacks of the conventional treatments for varicose veins, and satisfies the critical need for a minimally invasive and permanent treatment for varicose veins. The treatment of the present invention provides for complete obliteration of the affected veins without visible scarring, hospitalization or any of the other undesirable complications of the conventional treatments. In the detailed description that follows, like reference numerals are used to identify like elements in one or more of the figures.

Referring first to FIG. 1, the venous system of a leg 10 is illustrated. The venous system includes the deep veins 12 that lie close to the leg bones 15 and carry a majority of the blood, and the superficial veins 14 that lie close to the skin. The superficial veins 14 include the saphenous vein 16 and a plurality of tributary veins 18. As known in the art, these superficial veins 14 are most susceptible to the varicose vein condition since they are not well supported by muscle and are most visible due to their proximity to the skin.

A first step in treating varicose veins is to disconnect the saphenous vein 16 at its juncture with the femoral vein 22 (greater saphenous-femoral junction). This way, additional blood from the deep veins 12 will be prevented from backing into the saphenous vein 16, eliminating the primary cause of the varicose veins. While blood can still enter the saphenous vein 16 through the numerous tributary veins 18, the subsequent permanent closure of the saphenous vein (described below) will effectively prevent this occurrence. As in the prior art stripping technique, an incision in the groin area is necessary to disconnect the saphenous vein 16 (incision indicated as line segment A of FIG. 1). The saphenous vein 16 is located directly beneath a deep layer of the superficial fascia, and is normally ligated flush with the femoral vein 22. As will be understood from the description that follows, this groin incision will be the only one that requires suturing for closure and that may leave a scar; however, the proximity of the incision to the inguinal skin fold means that any incision scar will not be visible as a practical matter.

Alternatively, the saphenous vein 16 can be disconnected from the deep veins at a lower point along the leg, such as behind the knee at the lesser saphenous-popliteal junction. This alternative technique may be advisable in circumstances in which treatment of varicose veins is only necessary in the lower leg.

Figure 2:
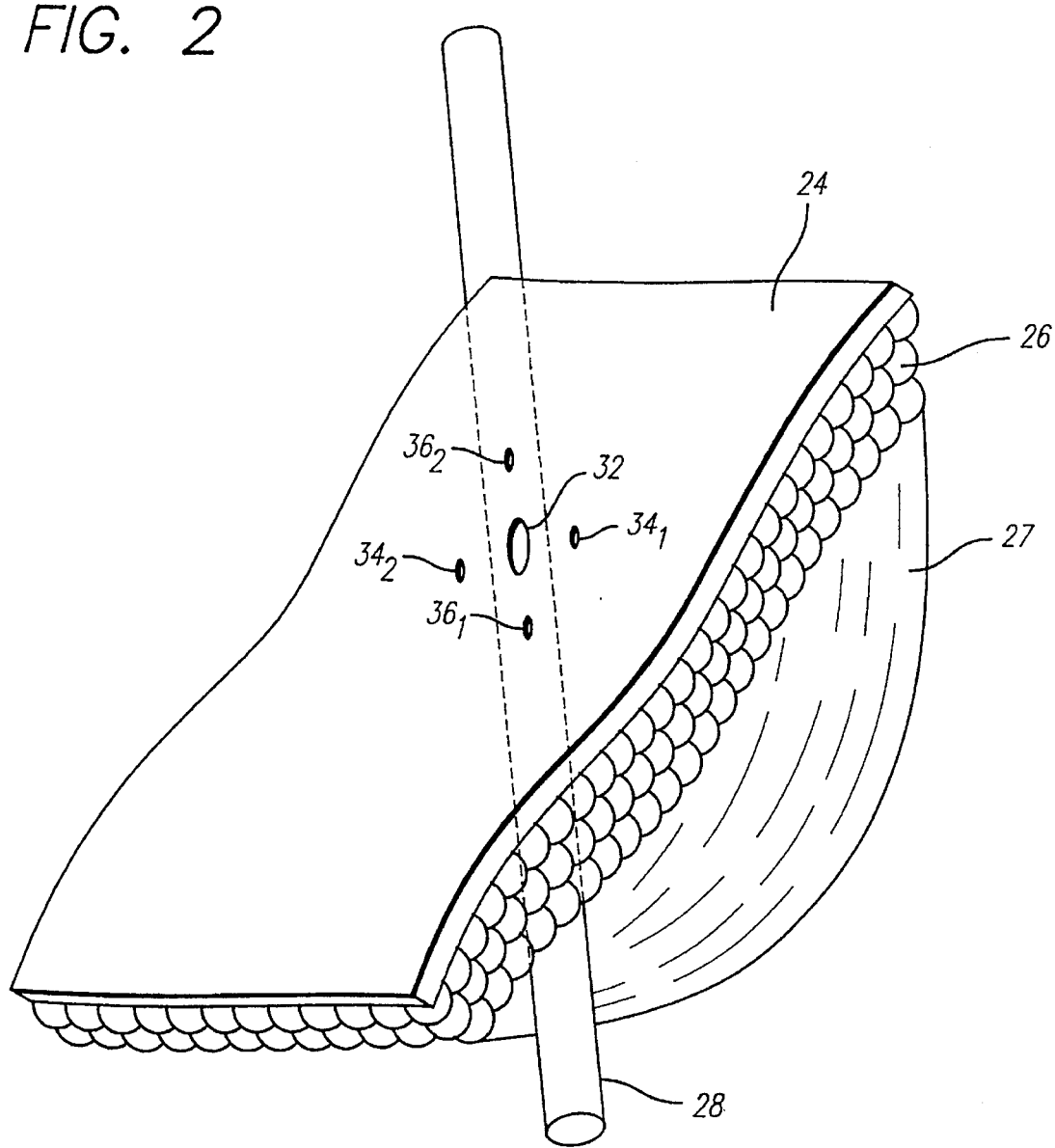
FIG. 2 is a partial perspective view of a portion of the leg showing the skin layer and a superficial vein.

Once the saphenous vein 16 is disconnected from the femoral vein 22, the varicose veins can be treated in accordance with the method of the present invention. Referring now to FIG. 2, a partial perspective view of a portion of the leg showing the skin layer 24, subcutaneous tissue 26 and a segment of a superficial vein 28 is illustrated. The superficial vein 28 lies between layers of subcutaneous tissue 26 and sartorius muscle 27. The specific segment of superficial vein 28 requiring treatment may comprise the saphenous vein 16 or one of the tributary veins 18, depending on the specific condition of the particular patient.

A plurality of small incisions are made through the skin layer 24 and subcutaneous tissue 26. These incisions include a main incision 32 that is centrally disposed over the vein 28, a pair of laterally disposed incisions $34_1$ and $34_2$ on either side of the main incision, and a pair of axially disposed incisions $36_1$ and $36_2$ on either end of the main incision (and also centrally disposed over the vein). Each one of these incisions 32, $34_1$, $34_2$, $36_1$, and $36_2$ are substantially smaller than the groin incision described above. The main incision 32 is larger and deeper than any of the others, and is on the order of ⅛ inch long. The laterally disposed incisions $34_1$ and $34_2$ and the axially disposed incisions $36_1$, and $36_2$ are on the order of 1/16 inch long, and only need be large enough to permit a needle carrying a suture to pass therethrough, as will be described below. The incisions may be made by a conventional precision micro-sized scalpel blade, such as a BEAVER™ blade.

Figure 3A:
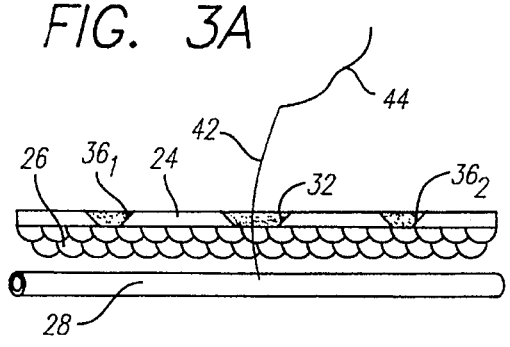
FIGS. 3A through 3F illustrate a minimally invasive surgical technique of the present invention for obstructing a superficial vein.

After completing the various incisions, the varicose vein is obstructed through the incisions. Referring now to FIGS. 3A through 3F, the steps for obstructing the vein 28 are illustrated. In FIG. 3A, a curved needle 42 carrying a supply of suture material 44 is inserted through the main incision 32 and subcutaneous tissue 26 until reaching the vein 28. It is anticipated that conventional suture material be utilized, such as comprised of TEFLON™. The extent of curvature of the needle 42 can be selected based upon the size, condition and placement of the vein 28 and/or the personal preference of the surgeon.

Figure 3B:
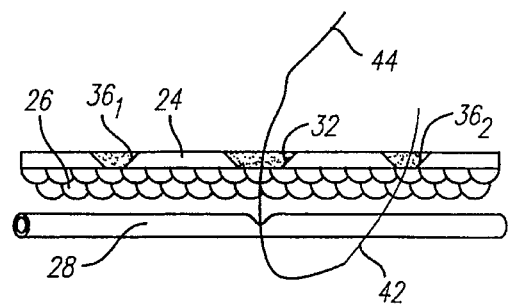
Figure 3C:
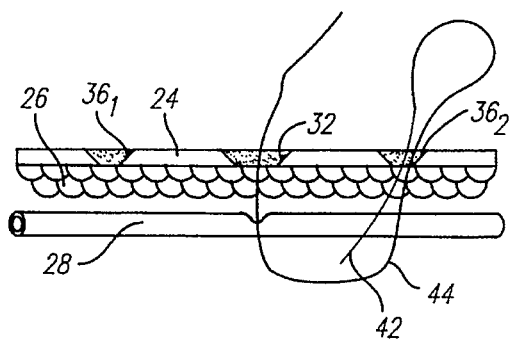
Figure 3D:
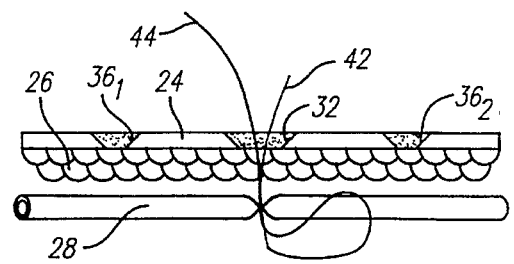
Figure 3E:
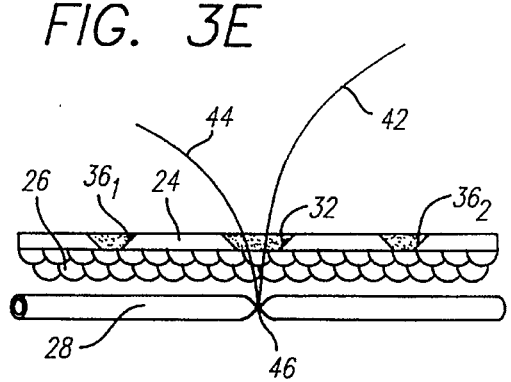
Figure 3F:
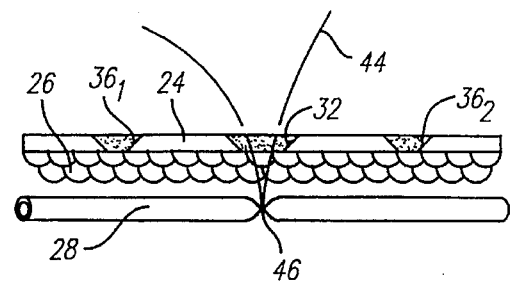

The needle 42 penetrates the wall of the vein and extends entirely through the vein to emerge at an opposite side of the vein. After drawing the needle 42 through the vein 28, the needle is withdrawn through one of the other incisions, such as the axially disposed incision $36_2$ as illustrated in FIG. 3B. Next, the needle 42 is re-threaded back through the same path. In FIG. 3C, the needle 42 is re-threaded through the axially disposed incision $36_2$, and in FIG. 3D, the needle penetrates through the vein 28 in the opposite direction from that described above. After passing through the vein 28, the needle 42 is re-withdrawn through the main incision 32, as illustrated in FIG. 3E. Once the needle 42 has exited the main incision 32, the suture material 44 can be pulled tight to remove any slack, and tied to a knot 46. The loose ends of the suture material 44 are then cut off, and the excess suture material pushed below the skin layer. The suturing steps are then repeated with respect to one or more of the other incisions $34_1$, $34_2$, and $36_1$. It should be apparent that the selection of incision $36_2$ as the first site for the suturing technique is for exemplary purposes only, and that any of the incisions $34_1$, $34_2$, $36_1$, and $36_2$ could be selected with subsequent incision sites selected in any desired order.

Figure 4:
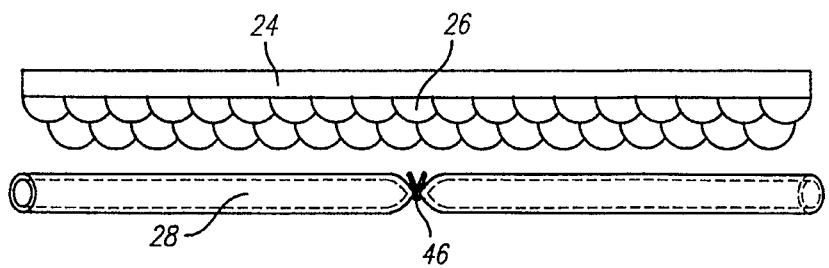
FIG. 4 illustrates a cross-sectional view of a skin layer and obstructed superficial vein.

Following the above suturing steps, the small incisions 32, $34_1$, $34_2$, $36_1$, and $36_2$ can be closed by conventional techniques, such as the use of sterile tape. While suturing of these incisions is also possible, it is considered unnecessary due to the small size of the incisions, and is also undesirable since suturing the skin can cause scarring. In FIG. 4, a cross-section of the skin layer 24 and an obstructed vein 28 after completion of the above technique is illustrated. As known in the art, even a partial obstruction of the vein 28 has the effect of permanently closing the vein. The patient's natural inflammation-repair response system will cause the vein to scar at the internal portion of the vein in the region of the knot 46, thus all blood flow through the vein will cease. Eventually, the pigmentation and swelling associated with the varicose vein condition will disappear. Since the suture material 44 does not protrude through the skin layer 24, the skin will heal smooth and have virtually no visible scarring. Moreover, the use of numerous passes of the suture material 44 through the vein 28 in association with one or more of the other incision sites causes the vein to lie flat under the skin 24, further insuring a cosmetically acceptable result.

In an alternative embodiment of the present invention, a tool is provided to increase the precision and rapidity of making the various incisions. FIGS. 5 and 6 illustrate the incision tool 50 having a base 52, a handle 54 and a plurality of blades 56, 58. The base 52 is substantially flat and has a plurality of sockets 55 extending perpendicularly inward into the base. The handle 54 has a curvature that matches the natural curvature of a surgeon's hand, so that it permits easy grasping and maneuvering of the tool 50. The sockets 55 allow the removable blades 56, 58 to be inserted therein. The centermost blade 58 protrudes from the base 52 to a greater extent than the other blades 56, but is otherwise identical to the other blades. Accordingly, the centermost blade 58 may be longer than the other blades 56, or its associated socket 55 may be shallower. The sockets 55 allow the surgeon to remove and dispose of the blades 56, 58 after use, so that the tool 50 can be subsequently sterilized and reused.

It should be apparent that the pattern of the blades 56, 58 protruding from the base 52 matches the incision pattern described above with respect to FIG. 2. To make the incisions of FIG. 2, the surgeon uses the tool 50 by simply pressing the base 52 against the patient's skin surface to allow the blades 56, 58 to penetrate through the skin layer 24. The tool 50 increases the surgeons control over the depth, accuracy and placement of the incisions, and thus reducing the time necessary to perform the operation. The surgeon would also be able to selectively configure the tool 50 by disposing blades in less than all the available sockets 55 so that the number and placement of incisions can be accurately controlled.

A second alternative embodiment of the present invention is illustrated in FIG. 7, and comprises a tool 60 for injecting a rivet or staple 80 into the varicose vein 28 to obstruct the vein. Stapling devices for surgically closing a wound are well-known in the art, and such devices could be modified to deliver a rivet or staple into the varicose vein 28. The tool 60 comprises a housing 62 having a grip portion 64 that is held by the surgeon. A trigger 66 operates an internal firing mechanism, that in simplified form includes a spring 74, a hammer 72 and a shaft 76. A cartridge 68 holds a supply of rivets 80, and sequentially feeds the individual rivets to the firing mechanism. A barrel 78 extends axially from the housing 62, and has a diameter similar to that of a syringe (note that the barrel 78 of FIG. 7 is not drawn to scale, but in practice would be substantially thinner than the housing 62.) The rivets 80 comprise a shaft 82 and a head 84, and are dimensioned to be fired through the barrel 78. It is anticipated that the rivets 80 be comprised of a flexible and non-reactive material, such as a plastic polymer, stainless steel or TEFLON™, that would enable the head 84 to compress during firing and return to a previous shape thereafter. Instead of the simplified mechanical arrangement of the firing mechanism described above, it should also be apparent that other well known mechanical or pneumatic mechanisms could be advantageously utilized.

FIGS. 8 and 9 illustrate a varicose vein treatment technique utilizing the tool 60 of FIG. 7. In FIG. 8, the barrel 78 is inserted through an incision 86 made through the skin layer 24. Alternatively, the barrel 78 may have a sharp point that enables it to be injected through the skin layer 24 without having to first make an incision. The tip of the barrel 78 is brought into proximity with the vein 28, and the firing mechanism is activated to propel the rivet 80 into the vein 28. The head of the rivet 80 prevents the rivet from passing entirely therethrough, and it remains lodged in the vein 28. The barrel 78 can then be withdrawn, and the incision 86 closed by use of conventional techniques, such as described above. The procedure can then be repeated at another location along the vein 28. As illustrated in FIG. 9, the obstruction of the vein 28 by the rivet 80 causes the vein to scar close. The use of the tool 60 reduces the need for numerous incisions at each closure site, and would further reduce the amount of time necessary to perform the operation.

Referring finally to FIG. 10, an alternative rivet 90 is illustrated. The rivet 90 has a head 92, a pointed tip 96 and a threaded shaft 94. The threaded rivet 90 can be inserted through an incision 86 to the superficial vein 28 as described above, but would be threaded into the vein as opposed to being forced through the wall of the vein. The tool 60 could be provided with a motor driven rotating barrel, as in conventional power screwdrivers. As described above, the rivet 90 would be comprised of a flexible and non-reactive material, such as a plastic polymer, stainless steel or TEFLON™.

Having thus described a preferred embodiment of a method and apparatus for treating varicose veins, it should be apparent to those skilled in the art that certain advantages of the within system have been achieved. It should also be appreciated that various modifications, adaptations, and alternative embodiments thereof may be made within the scope and spirit of the present invention. The invention is further defined by the following claims.

What is claimed is:

1. A minimally invasive method for treating a varicose vein, comprising the steps of:

ligating the junction between said vein and deep veins of the patient's leg;

opening at least one small incision through a skin layer adjacent to a varicose region of said vein;

at least partially obstructing said vein through said at least one small incision; and closing said at least one small incision.

2. The method of claim 1, wherein said at least partially obstructing step further comprises threading a suture through said at least one small incision that extends through at least a portion of said vein.

3. The method of claim 1, wherein said opening step further comprises opening a plurality of small incisions in close proximity with said vein with at least one of said plurality of small incisions being substantially centered over said vein.

4. The method of claim 3, wherein said at least partially obstructing step further comprises the steps of:

threading a suture through said at least one substantially centered incision so that said suture penetrates through at least a portion of said vein;

withdrawing said suture through another one of said plurality of small incisions;

re-threading said suture through said another one of said plurality of small incision so that said suture penetrates through at least a portion of said vein in close proximity with said portion of said vein previously penetrated by said suture; and re-withdrawing said suture through said at least one substantially centered incision.

5. The method of claim 4, further comprising the step of repeating said threading, withdrawing, re-threading, and re-withdrawing steps with respect to at least one other one of said plurality of small incisions.

6. The method of claim 4, further comprising the step of tying exposed ends of said suture that extend outwardly of said vein through said at least one substantially centered incision.

7. The method of claim 6, further comprising the step of cutting said exposed ends of said suture that extend outwardly of said vein through said at least one substantially centered incision.

8. The method of claim 7, wherein said closing step further comprises the step of preventing any portion of said cut exposed ends of said suture from extending through said at least one substantially centered incision.

9. The method of claim 1, wherein said at least partially obstructing step further comprises injecting a rivet through said at least one small incision that extends through at least a portion of said vein.

\* \* \* \* \*